United States Patent
Cleek et al.

(10) Patent No.: US 10,314,783 B2
(45) Date of Patent: Jun. 11, 2019

(54) ARTICLES AND METHODS OF TREATING VASCULAR CONDITIONS

(71) Applicant: W. L. Gore & Associates, Inc., Newark, DE (US)

(72) Inventors: Robert L. Cleek, Flagstaff, AZ (US); Paul D. Drumheller, Flagstaff, AZ (US); Theresa A. Holland, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 248 days.

(21) Appl. No.: 14/466,459

(22) Filed: Aug. 22, 2014

(65) Prior Publication Data

US 2014/0364404 A1  Dec. 11, 2014

Related U.S. Application Data

(62) Division of application No. 12/404,083, filed on Mar. 13, 2009, now abandoned.

(51) Int. Cl.
*A61K 9/00* (2006.01)
*A61K 9/06* (2006.01)
(Continued)

(52) U.S. Cl.
CPC ............. *A61K 9/06* (2013.01); *A61K 9/0024* (2013.01); *A61K 31/565* (2013.01); *A61K 31/573* (2013.01); *A61K 45/06* (2013.01); *A61K 47/10* (2013.01); *A61K 47/26* (2013.01); *A61K 47/32* (2013.01); *A61K 47/36* (2013.01); *A61K 47/40* (2013.01); *A61L 27/50* (2013.01); *A61L 27/52* (2013.01); *A61L 27/54* (2013.01); *A61L 29/14* (2013.01); *A61L 29/145* (2013.01);
(Continued)

(58) Field of Classification Search
CPC .... A61K 31/565; A61K 31/573; A61K 45/06; A61K 47/10; A61K 47/26; A61K 47/32; A61K 47/36; A61K 47/40; A61K 9/0024; A61K 9/06; A61L 2300/415; A61L 2300/802; A61L 27/50; A61L 27/52; A61L 27/54; A61L 29/14; A61L 29/145; A61L 29/16
USPC ........ 514/180, 182, 183, 312, 411; 614/507, 614/508, 509; 424/488
See application file for complete search history.

(56) References Cited

U.S. PATENT DOCUMENTS 5,102,402 A  4/1992  Dror et al.
5,171,217 A  12/1992  March et al.
(Continued)

FOREIGN PATENT DOCUMENTS

WO  01/54748  8/2001

OTHER PUBLICATIONS

Subbotin (Analysis of arterial intimal hyperplasia: review and hypothesis, Theoretical Biology and Medical Modelling (2007) 4:1-41) (Year: 2007).*

(Continued)

*Primary Examiner* — Brian-Yong S Kwon
*Assistant Examiner* — Miriam A Levin

(57) ABSTRACT

The present invention relates to articles and methods of treating vascular conditions with a thixotropic, turbid, bioactive agent-containing gel material capable of being essentially removed from an implantation site upon re-establishment of fluid flow at the implantation site.

19 Claims, 7 Drawing Sheets

| Dwell Time (min) | # Canines | Retention (μg dexamethasone / g tissue) | | |
|---|---|---|---|---|
| | | Avg. | ± | St. Dev. |
| 2 | 3 | 9.3 | ± | 3.9 |
| 10 | 3 | 10.6 | ± | 5.9 |
| 40 | 2 | 13.9 | ± | 7.0 |

(51) Int. Cl.

| | | |
|---|---|---|
| *A61K 45/06* | (2006.01) | |
| *A61K 47/10* | (2017.01) | |
| *A61K 47/26* | (2006.01) | |
| *A61K 47/40* | (2006.01) | |
| *A61L 27/50* | (2006.01) | |
| *A61L 27/52* | (2006.01) | |
| *A61L 27/54* | (2006.01) | |
| *A61L 29/14* | (2006.01) | |
| *A61L 29/16* | (2006.01) | |
| *A61K 31/565* | (2006.01) | |
| *A61K 31/573* | (2006.01) | |
| *A61K 47/32* | (2006.01) | |
| *A61K 47/36* | (2006.01) | |

(52) U.S. Cl.
CPC ......... *A61L 29/16* (2013.01); *A61L 2300/416* (2013.01); *A61L 2300/802* (2013.01)

(56) References Cited

U.S. PATENT DOCUMENTS

| | | | |
|---|---|---|---|
| 5,213,580 A | 5/1993 | Slepian et al. | |
| 5,527,532 A | 6/1996 | Edelman | |
| 5,538,504 A | 7/1996 | Linden et al. | |
| 5,674,287 A | 10/1997 | Slepian et al. | |
| 5,749,922 A | 5/1998 | Slepian et al. | |
| 5,800,538 A | 9/1998 | Slepian et al. | |
| 5,893,839 A | 4/1999 | Johnson | |
| 6,290,729 B1* | 9/2001 | Slepian | A61F 2/062 623/23.72 |
| 6,726,923 B2 | 4/2004 | Iyer | |
| 6,730,313 B2 | 5/2004 | Helmus et al. | |
| 6,818,018 B1* | 11/2004 | Sawhney | A61L 27/34 523/113 |
| 6,860,867 B2 | 3/2005 | Seward et al. | |
| 2002/0019369 A1 | 2/2002 | Li et al. | |
| 2004/0072799 A1 | 4/2004 | Li et al. | |
| 2006/0198976 A1 | 9/2006 | Trapp | |
| 2007/0141109 A1* | 6/2007 | Chadrasekar | A61K 31/565 424/423 |
| 2007/0218118 A1* | 9/2007 | Michal | A61K 9/0024 424/450 |
| 2008/0045985 A1* | 2/2008 | Gurtner | A61B 17/00491 606/154 |

OTHER PUBLICATIONS

Harada A, Kamachi M. Complex formation between poly(ethylene glycol) and α-cyclodextrin. Macromolecules 1990; 23:2821-2823.

Harada A, Li J, Kamachi M. Preparation and properties of inclusion complexes of poly(ethylene glycol) with α-cyclodextrin. Macromolecules 1993; 26:5698-5703.

Li J, Ni X, Leong K. Injectable drug-delivery systems based on supramolecular hydrogels fromed by poly(ethylene oxide)s and α-cyclodextrin Biomed Mater Res, 2003; 65:196-202.

Minton A, Barnett M, Cosslett A. Detection of particulate material in parenteral nutrition admixtures. Nutrition 1998; 14:251-252.

Nemec K, Kopelent-Frank H, Greif R. Standardization of infusion solutions to reduce the risk of incompatibility. Am J Health Syst Pharm 2008; 65:1648-1654.

Tian F, Zhang B, Zhao X, et al. In vitro evaluation of embolization effects of thermosensitive N-isopropylacrylamide-based copolymer solutions. Polym Int 2006; 55:405-408.

Trissel L, Martinez J. Turbidimetric assessment of the compatibility of taxol with 42 other drugs during simulated Y-site injection. Am J Hosp Pharm 1993; 50:300-304.

Wong J, Brugger A, Khare A, et al. Suspensions for intravenous (IV) injection: a review of development, preclinical and clinical aspects, Adv Drug Del Rev 2008; 60:939-954.

Fram et al. Localized Intramural Drug Delivery During Balloon Angioplasty Using Hydrogel-Coated Balloons and Pressure-Augmented Diffusion. JACC 1994; vol. 23 (7), 1570-1577.

* cited by examiner

| Dwell Time (min) | # Canines | Retention (μg dexamethasone / g tissue) | | |
|---|---|---|---|---|
| | | Avg. | ± | St. Dev. |
| 2 | 3 | 9.3 | ± | 3.9 |
| 10 | 3 | 10.6 | ± | 5.9 |
| 40 | 2 | 13.9 | ± | 7.0 |

| Time of Vessel Harvest | # Canines | Retention (µg estradiol/ g tissue) | | |
|---|---|---|---|---|
| | | Avg. | ± | St. Dev. |
| 14 d | 3 | 0.3 | ± | 0.3 |
| 1 h | 3 | 9.8 | ± | 13.1 |

FIG. 4

ARTICLES AND METHODS OF TREATING VASCULAR CONDITIONS

FIELD OF THE INVENTION

The present invention relates to articles and methods of vascular-based therapies to treat a variety of vascular conditions.

BACKGROUND OF THE INVENTION

Vascular conditions arise from a variety of causes, and in some cases, necessitate surgical or endovascular intervention. Trauma to the vascular system may also necessitate surgical intervention to treat the traumatized anatomy. The long-term implantation of vascular prostheses including vascular grafts, stent-grafts, and stents, and the application of treatment modalities, including balloon angioplasty are often undertaken to treat vascular conditions including vascular disease and vascular trauma.

Consequences of surgical intervention have been observed following implantation of vascular prostheses including vascular grafts, stent-grafts, stents, and other prostheses, particularly when an anastomosis is formed. The consequences of surgical intervention include, but are not limited to, inflammation, intimal hyperplasia, stenosis, and restenosis of the treated blood vessel near the formed anastomosis. Inflammation is a physiological response by a mammalian body to surgery, injury, irritation, or infection. An inflammatory response involves complex biological activities at chemical, cellular, tissue, and organ levels. Generally, an inflammatory response is a protective attempt to remove an injurious stimulus, as well as to initiate a healing process for the diseased or traumatized tissue. Intimal hyperplasia is a pathological condition in which an overabundant inflammatory response is initiated involving stimulation, migration, and proliferation of numerous cell types. Stenosis and restenosis are constrictions of the blood vessel lumen and may be caused by mechanisms including, but not limited to, compliance mismatch between the native vessel and the implanted vascular prosthesis, host tissue response to an implanted material, prior disease states, and infection. Stenosis and restenosis can progress to a point where additional surgical intervention is required to enlarge the blood vessel lumen diameter of the blood vessel or the implanted vascular prosthesis to establish a less restrictive conduit for blood flow.

Additional vascular conditions that may require surgical or endovascular intervention include, but are not limited to, vascular injury, vascular prophylactic intervention, vascular disease, phlebitis, intimal hyperplasia, vulnerable plaques, carotid plaques, coronary plaque, vascular plaque, aneurismal disease, vascular dissections, atherosclerotic plaques, atherosclerotic lesions, vascular infection, and vascular sepsis.

One approach to treatment of these vascular conditions involves local delivery of a suitable pharmaceutical or biologically active agent in a liquid vehicle within luminal spaces of a blood vessel at or near the site of the vascular condition. The liquid vehicle containing the pharmaceutical or biologically active agent is contacted with tissues of the luminal space at a vascular treatment site for a determined length of time (dwell time). However, this approach often requires extensive dwell times at the vascular treatment site to ensure adequate delivery and retention of the bioactive agent at the vascular treatment site to treat the vascular condition. Even with extensive dwell times, the delivery and retention of the bioactive agent at the vascular treatment site using this approach may be insufficient to treat the vascular condition.

Another therapeutic approach is the implantation of vascular prostheses having a pharmaceutical-containing coating to deliver a pharmaceutical to a lumen of a blood vessel or other vascular conduit. Examples of vascular prostheses having a pharmaceutical-containing coating include, but are not limited to, stents, stent grafts, grafts, and angioplasty balloons. Other examples of vascular prostheses having a pharmaceutical-containing coating are drug eluting stents and drug eluting stent grafts (DESs). DESs are used in the treatment of coronary artery disease and peripheral artery disease. A high degree of physician skill is often required to implant DESs without damaging or traumatizing surrounding vascular tissue. The treatment of a vascular condition by the implantation of DESs may require long term implantation of the vascular prosthesis. The long term implantation of the vascular prosthesis may also result in mechanical trauma to the vascular treatment site due to a nonlubricious nature of the pharmaceutical-containing coating. The long term implantation of the vascular prosthesis may also result in an unwanted tissue reaction at the vascular treatment site due to the components of the vascular prosthesis and/or the pharmaceutical-containing coating. Therefore it is desirable to have an improved method for treating vascular conditions that requires minimal physician skill to perform. It is desirable to have an improved method for treating vascular conditions that avoids long term implants.

Drug eluting balloons (DEBs) are additional examples of vascular prostheses having a pharmaceutical-containing coating. The literature discloses the use of DEBs for the treatment of coronary artery disease and peripheral artery disease (see e.g., U.S. Pat. No. 5,102,402, issued to Dror et al.). Dror et al. disclose placing a DEBs in a blood vessel lumen to treat the vessel wall, inflating the balloon, and contacting the balloon surface with the luminal vessel wall to deliver a pharmaceutical into the blood vessel wall. Another example of treatment using DEBs involves an angioplasty balloon having microneedles (see e.g., U.S. Pat. Nos. 5,171,217; 5,538,504; and 6,860,867). DEBs often require a high degree of physician skill to implement. The implantation of the DEBs may also result in mechanical trauma to the vascular treatment site due to the components of the DEBs and/or the pharmaceutical-containing coating. It is desirable to have improved methods for treating and preventing vascular conditions that are simple and easy to implement. It is also desirable to have methods for treating and preventing vascular conditions that avoid mechanical trauma to the vascular treatment site and are compatible with the delivery of a wide variety of pharmaceuticals.

In addition to delivering drugs to blood vessels from stents, stent-grafts, grafts, and other prostheses, intraluminal drug delivery methods include methods that chemically "pave" luminal surfaces of a blood vessel (see e.g., U.S. Pat. Nos. 5,213,580; 5,674,287; 5,749,922; and 5,800,538). These "paving" methods involve fixation, polymerization, and bonding of a drug delivery system to the lumen of a blood vessel. Degradation of such delivery systems ranges from days to weeks. The methods can be challenging as they involve chemical reactions with the blood vessel lumen. These chemical reactions may induce trauma to the vascular treatment site. It is desirable to have improved methods for treating and preventing vascular conditions which avoid "paving" of the luminal surfaces of the blood vessel.

Methods of delivering drugs to perivascular locations are described. U.S. Pat. No. 6,726,923, issued to Iyer, and U.S.

Pat. No. 5,527,532, issued to Edelman, disclose perivascular drug eluting wraps and matrices applied to adventitial surfaces of a blood vessel to treat vascular inflammation.

U.S. Pat. No. 5,893,839, issued to Johnson, discloses a method of treating restenosis involving the delivery of a biologically active substance percutaneously.

U.S. Pat. No. 6,730,313, issued to Helmus et al., discloses a method for treating intimal hyperplasia involving contacting an exterior surface of a blood vessel with a "flowable" drug delivery vehicle.

These methods usually require complex procedural techniques, often implemented through invasive surgical techniques. In addition, these methods may require long term implantation of a vascular prosthesis, drug eluting wraps, matrices, and flowable drug delivery vehicles. Long term implantation of the vascular prosthesis, drug eluting wraps, matrices, and flowable drug delivery vehicles may also result in an unwanted tissue reaction at the vascular treatment site due to the nature of their components. It is desirable to have improved methods for treating and preventing vascular conditions that allow delivery of a wide variety of pharmaceuticals and biologics to diseased or traumatized vascular tissue without the need for long term implants, that are easily implemented, and that are applied through surgical and endovascular techniques.

Li et al. (U.S. Patent Application Publication 2002/0019369) disclose an injectable cyclodextrin polymer-based composition made from cyclodextrin, polyethylene glycol, and a pharmacologically effective amount of at least one drug. Li et al. further disclose their composition can be used subcutaneously, intramuscularly, intradermally, or intracranially. However, Li et al. do not teach their composition can be injected into the vasculature or into flowing blood.

As is disclosed to the literature, compositions made of cyclodextrin and polyethylene glycol form inclusion complexes. The inclusion complexes have the form of hydrogels, turbid solutions, and precipitates (Li, J Biomed Mater Res, 65A, 196, 2003; Harada, Macromolecules, 26, 5698, 1993; Harada, Macromolecules, 23, 2821, 1990).

Indeed, as indicated by the literature, injection of particles in the form of hydrogel materials, turbid solutions, and precipitates into the vasculature or into flowing blood can have adverse consequences, including decreased drug effectiveness, phlebitis, embolism, and blockage of capillaries (Nemec, Am J Heath Syst Pharm, 65, 1648, 2008; Wong, Adv Drug Del Rev, 60, 939, 2008; Minton, Nutrition, 14, 251, 1998; Tian, Polym Int, 55, 405, 2006). Instructions for use of an injectable pharmaceutical solution contraindicate injection into the vasculature or flowing blood if the injectable pharmaceutical solution is turbid or contains precipitates.

There remains a need for improved vascular-based therapies to treat a variety of vascular conditions. The improved therapies would be easily implemented and would obviate mechanically or chemically induced trauma to the vascular treatment site. The improved therapies would allow for administration of thixotropic, turbid, bioactive agent-containing gel materials to vascular tissue at a vascular treatment site. The gel material would readily release one or more bioactive agents contained by the gel material to vascular tissue in need of treatment or repair. The gel material would dissolve in the flowing blood without occluding vascular structures located distally (i.e., downstream) to the administration site. The therapies could be applied prophylactically, interventionally, surgically, or endovascularly.

SUMMARY OF THE INVENTION

The present invention relates to methods of treating or preventing a vascular condition with a thixotropic, turbid, bioactive agent-containing gel material. The method can also be used to treat or repair traumatized vascular structures. The gel material will readily deliver one or more bioactive agents contained by the gel material to a diseased or disease-prone vascular treatment site in need of treatment or repair. In the method, the gel material is capable of being directly injected into luminal spaces of blood vessels and other fluid-conducting anatomical structures with little or no mechanical or chemical trauma to vascular tissues of the vascular treatment site. After contact with the vascular tissues, the gel material will substantially dissolve in flowing blood without occluding vascular structures located distally (i.e., downstream) to the administration site. The method could be applied prophylactically, interventionally, surgically, or endovascularly. The method does not require a high degree of skill to perform. On the contrary, the method relies on simple injection of the gel material within a vascular structure for delivery of a pharmaceutical or other bioactive agent to vascular tissue in need of treatment.

The gel material used in the method is a thixotropic, turbid, gel material, having high viscosity at low shear, and therefore, coherently resides in luminal spaces of a blood vessel under conditions of low or no blood flow. Upon resumption of flowing blood in the treated blood vessel, the resultant fluid shear force converts the gel material to a low viscosity, blood-soluble composition that is substantially dissolved in flowing blood. Consequently, the gel material is readily and essentially removed from the vascular treatment site upon re-establishment of flowing blood without obstructing vascular structures located downstream of the treatment site.

The method allows for surgical, endovascular, and minimally-invasive delivery of a wide variety of pharmaceuticals and biologics for prophylactic and interventional vascular therapy. Preferred bioactive agents are pharmacologically and biologically active entities that inhibit a variety of vascular pathologies including, but not limited to, intimal hyperplasia. The gel material can be delivered through needle and catheter based devices including, but not limited to, balloon catheters, infusion catheters, and micro-injection systems. In addition to placement of the gel material within a blood conduit, the composition can be applied to blood contacting surfaces of medical devices, including, but not limited to, vascular grafts, stents, stent-grafts, and balloons.

One embodiment of the present invention relates to a method of treating a vascular condition by providing a thixotropic, turbid, gel material containing at least one bioactive agent capable of treating vascular tissue in sufficient amounts to treat said vascular condition in said vascular tissue upon release of said bioactive agent from said gel material, administering said gel material to a vascular treatment site within an interior space of a blood vessel, and allowing said gel material to remain at said vascular treatment site for a dwell time sufficient to release said bioactive agent from said gel material. In addition, the gel material does not occlude vascular structures upon introduction into flowing blood.

Another embodiment of the present invention relates to a method of treating a vascular condition by providing a thixotropic, turbid, gel material containing at least one bioactive agent capable of treating intimal hyperplasia in sufficient amounts to inhibit intimal hyperplasia upon release of said bioactive agent from said gel material, administering said gel material to a vascular treatment site within an interior space of a blood vessel, and allowing said gel material to remain at said vascular treatment site for a dwell time sufficient to release said bioactive agent from said gel material. In addition, the gel material does not occlude vascular structures upon introduction into flowing blood.

Another embodiment of the present invention relates to a method of treating a vascular condition by providing a cyclodextrin polymer-based composition comprising cyclodextrin, a polymer, and a pharmacologically effective amount of at least one drug; wherein the polymer comprises ethylene glycol units that can form a hydrogel with the cyclodextrin, wherein the cyclodextrin and the polymer self-assemble to form a hydrogel by spontaneous association and are present in the composition in respective amounts effective to make the hydrogel thixotropic and injectable into the body of a person through a needle, and wherein the hydrogel forms a matrix for the drug such that when the composition is injected into the body of the person, the drug is released from the hydrogel in a sustained manner, administering said hydrogel material to a vascular treatment site within an interior space of a blood vessel, and allowing said hydrogel material to remain at said vascular treatment site for a dwell time sufficient to release said bioactive agent from said hydrogel material.

Other embodiments of the present invention relate to medical devices having thixotropic, turbid, gel materials, as described herein, applied to at least a portion of the medical device. The medical devices are either implantable devices or are devices used to deliver one or more bioactive agents to a specific site in the body. A preferred medical device of the present invention comprises a cyclodextrin polymer-based composition comprising cyclodextrin, a polymer, and a pharmacologically effective amount of at least one drug, wherein the polymer comprises ethylene glycol units that can form a hydrogel with the cyclodextrin, wherein the cyclodextrin and the polymer self-assemble to form a hydrogel by spontaneous association and are present in the composition in respective amounts effective to make the hydrogel thixotropic, and wherein said hydrogel is attached, or otherwise applied, to at least a portion of a medical device. Further embodiments include at least one bioactive agent combined with the hydrogel. Preferably, the bioactive agent is capable of treating vascular tissue and is present in the hydrogel in sufficient amounts to treat a vascular condition upon release of the bioactive agent from the hydrogel combined therewith.

Other features and advantages of the invention will be apparent from the following description and from the claims.

BRIEF DESCRIPTION OF THE DRAWINGS

FIG. 1 shows a table of data.
FIG. 4 shows a table of data.

DETAILED DESCRIPTION OF THE INVENTION

Figure 2:
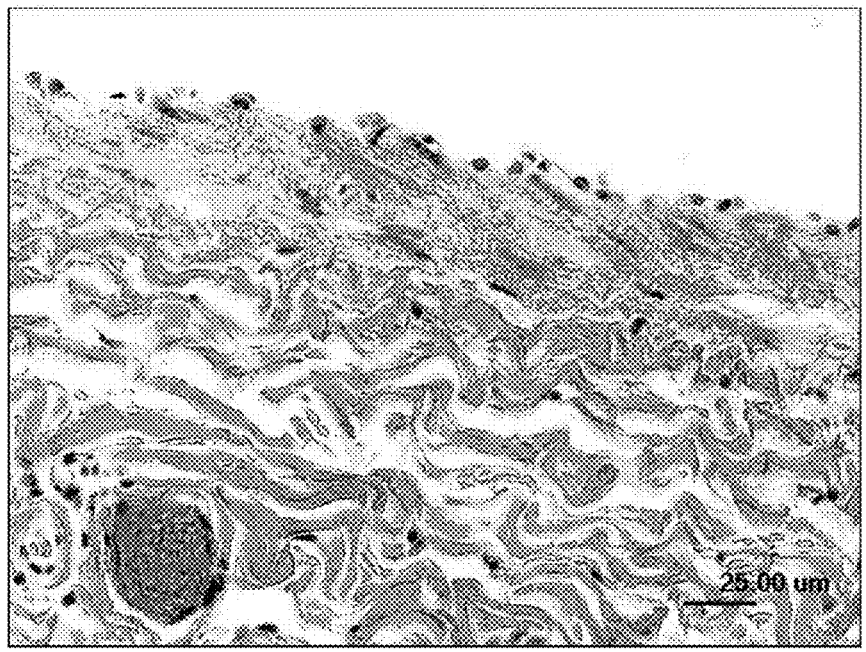
FIG. 2 shows two photographs (a) and (b), each containing histological data.
Figure 2:
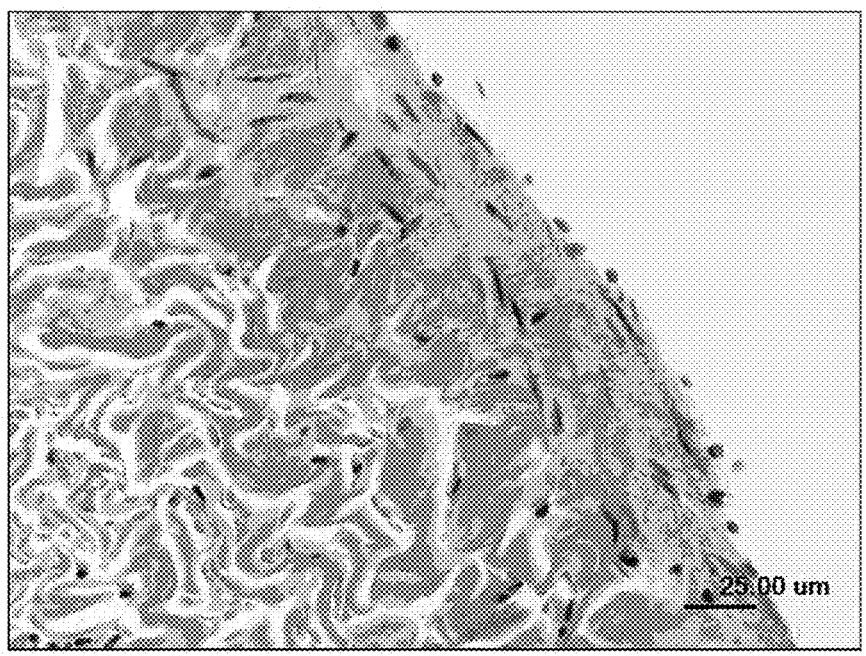

The present invention relates to methods of treating or preventing a vascular condition with a thixotropic, turbid, bioactive agent-containing gel material.

The invention utilizes turbid gel materials having thixotropic properties. The thixotropic properties of the gel materials permit the compositions to undergo changes in viscosity in response to the presence or absence of shear forces applied to the compositions. When a shear force is applied to the gel material by injection of the gel material from a needle-containing syringe, the viscosity of the composition is altered to a point where the composition can easily pass through the needle-containing syringe. When the shear force is removed from the gel material, the viscosity of the composition is altered to a point where the composition will not flow under the influence of its own weight. A suitable gel material for use in the present invention is a material that can be made to flow under shear force, but exhibits no flow under the influence of its own weight under non-shear conditions.

When the gel material containing a bioactive agent is placed inside a blood vessel to form an indwelling composition, the bioactive agent moves from the indwelling composition to tissues of the blood vessel—independent of the viscosity of the gel material Once sufficient time has elapsed for a desired amount of bioactive agent to be delivered from the indwelling composition to a vascular treatment site in need of treatment or repair, the indwelling composition is exposed to shear forces to decrease the viscosity of the gel material and begin a process of dissolution of the gel material into flowing blood. In the present invention, shear force is applied to the indwelling composition by permitting blood to flow through the vascular treatment site containing the indwelling composition. As the viscosity of the gel material is reduced, the indwelling composition begins to substantially dissolve in the flowing blood. Substantial dissolution of the gel material in flowing blood continues until essentially all of the gel material has been removed from the treatment site and is present in a substantially to completely dissolved state in flowing blood. Once present in flowing blood, the gel material does not diminish, limit, occlude, or otherwise interfere with the flow of blood in vascular structures located distally (i.e., downstream) to the vascular treatment site.

In a preferred embodiment, a thixotropic, turbid, bioactive agent-containing gel material is administered to a vascular treatment site within an isolated interior space of an exsanguinated fluid conduit. The gel material is allowed to reside in the isolated interior space for a period of time ("dwell time"). The dwell time for the gel material is primarily determined by the rate at which a bioactive agent is delivered from the gel material to vascular tissues at a treatment site. The dwell time for the gel material can also be determined by the timing and sequencing of a similar procedure at another vascular treatment site or other medical procedures being performed at the same time. Transfer of bioactive agents from a gel material used in the present invention to vascular and other tissues occurs in a range of about 5 seconds to greater than about one hour. Regardless of the delivery rate of bioactive agents to a vascular treatment site in need of treatment by the present invention, a similar or different surgical procedure to another vascular treatment site can increase the dwell time of the gel material at the vascular tissue treatment site.

Once sufficient bioactive agent has been delivered to a vascular treatment site in need of treatment according to methods of the present invention, blood is allowed to re-enter the isolated interior space of the fluid conduit. Shear forces applied to the thixotropic gel material by the flowing blood cause the viscosity of the indwelling composition to decrease. The decrease in viscosity of the gel material causes the indwelling composition to dissolve substantially in blood flowing through the treated fluid conduit. Substantial dissolution of the gel material in flowing blood is sufficient to prevent blockage, or occlusion, of vascular structures located distally (i.e., downstream) of the vascular treatment site.

A "gel material" is a material that includes at least two components, a solvent component and a polymer chain component. The term "hydrogel" as used herein means a material that includes at least two components, an aqueous solvent component, and a polymer chain component. The gel material of the present invention does not flow under the influence of its own weight. This property is observable by the unaided eye when about 5 ml of gel material is placed into a 13 mm by 100 mm standard glass test tube and inverted 180 degrees for a few seconds.

In addition to thixotropy, the gel material employed in the present invention is turbid. The term "turbid" means the gel material appears hazy, translucent, cloudy, opalescent, or opaque to the unaided eye. The turbidity of gel materials used in the present invention can be determined when about 5 ml of gel material is placed into a 13 mm by 100 mm standard glass test tube and viewed by the unaided eye at a right angle to an illuminating light source and against a dark background.

The terms "thixotropic" and "thixotropy" refer to physical properties of particular chemical entities. A chemical entity is thixotropic when the chemical entity exhibits behavior in which viscosity of the chemical entity decreases under an applied shear force and then increases in viscosity when the applied shear force is removed. Shear forces can be applied to thixotropic gel materials by methods including, but not limited to, shaking, stirring, exposure to fluid flow, and mechanical expansion in surface area. Thixotropy can be assessed using methods such as rheometry and viscometry.

The term "vascular condition" includes, but is not limited to, vascular injury, vascular prophylactic intervention, vascular disease, intimal hyperplasia, phlebitis, vulnerable plaques, carotid plaques, coronary plaque, vascular plaque, aneurismal disease, vascular dissections, atherosclerotic plaques, atherosclerotic lesions, vascular infection, and vascular sepsis.

The term "inflammation" as used herein refers to a physiological response by a mammalian body to surgery, injury, irritation, or infection. An inflammatory response involves complex biological activities at chemical, cellular, tissue, and organ levels. Generally, an inflammatory response is a protective attempt to remove an injurious stimulus, as well as to initiate a healing process for the diseased or traumatized tissue.

Suitable polymer chain components for the thixotropic turbid gel materials in the present invention are natural and synthetic polymers that are capable of forming a thixotropic, turbid, gel. The polymer chain components include but are not limited to polyethers such as polyethylene glycol, polypropylene glycol, poly(ethylene glycol-co-propylene glycol), copolymers of polyethylene glycol, and copolymers of polypropylene glycol; polyols such as polyvinyl alcohol and polyallyl alcohol; polyanions such as polyacrylic acid and poly(methacrylic acid); polyanionic polysaccharides such as alginate, heparin, heparin sulfate, dextran sulfate, xanthan, carrageenan, gum arabic, tragacanth, arabinogalactan, and pectin; neutral polysaccharides such as agar, agarose, hyaluronic acid, carboxymethylcellulose, and dextran; macrocyclic polysaccharides such as cyclodextrin and hydroxypropyl cyclodextrin; polycations such as poly(lysine), poly(allylamine), poly(ethyleneimine), poly(guanidine), poly(vinyl amine), $\alpha,\omega$-polyethylene glycol-diamine, and poly(quaternary amine); polyanionic polysaccharides such as chitin and chitosan; polyacrylonitriles such as hydrolyzed polyacrylonitrile, poly(acrylamide-co-acrylonitrile), and their copolymers; and protein based polymers such as gelatin, collagen, thrombin, and fibrin.

In one embodiment, the gel materials are composed of $\alpha$-cyclodextrin ($\alpha$CD) and polyethylene glycol (PEG). Such gel materials are thixotropic and turbid.

Suitable bioactive agents in the thixotropic turbid gel materials in the present invention are biologically and pharmaceutically active entities that exert a desired effect upon the native cells, microbes, intercellular environments, and tissues of the vascular treatment site. The gel material may include a solubilizing agent to improve or otherwise alter the solubility of the bioactive agent in the gel material. The gel material may include a permeability agent to improve or otherwise alter the delivery of the bioactive active agent to vascular tissues. The bioactive agent may consist of simple molecules, macromolecules, inorganic molecules, and complex biological entities such as cells, tissues, or tissue aggregates.

Bioactive agents suitable for use in the present invention include, but are not limited to, protein based molecules such as enzymes, growth factors, proteases, glycoproteins, and cytokines; nucleic acid based molecules such as DNA, RNA, genes, gene fragments, ribozymes, and nucleic acids; carbohydrate based molecules such as glucose, glycogen, cyclodextrin, and heparin; lipid based molecules such as cholesterol and prostaglandin; complex biological entities such as extracellular matrix, viruses, virenos, prions, cells, tissues, and tissue aggregates; and organic molecules such as hormones, organic catalysts, organometallics, and oleophobics. Other bioactive agents include drugs including, but not limited to, cardiovascular agents, chemotherapeutics, antimicrobials, antibiotics, anesthetics, anticoagulants, hemostatics, antihistamines, antitumors, antilipids, antifungals, antimycotics, antipyretics, vasodilators, hypertensive agents, oxygen free radical scavengers, antivirals, analgesics, antiproliferatives, antiinflammatories, diagnostic agents, visualization agents, angiographic contrast agents, phase contrast agents, and radiopaque agents. Other bioactive agents include but are not limited to antirestenotic drugs including, but not limited, to pimecrolimus, cytochalasin, dicumarol, cyclosporine, latrunculin A, methotrexate, tacrolimus, halofuginone, mycophenolic acid, genistein, batimistat, dexamethasone, cudraflavone, simvastatin, prednisolone, doxorubicin, bromopyruvic acid, carvedilol, mitoxantrone, tranilast, etoposide, hirudin, trapidil, mitomycin C, abciximab, cilostazol, irinotecan, estradiol, diaziquone, dipyridamole, melatonin, colchicine, nifedipine, vitamin E, paclitaxol, diltiazem, vinblastine, verapamil, vincristine, rapamycin, angiopeptin, everolimus, heat shock proteins, zotarolimus, nitroglycerin, and prednisone.

Bioactive agents used in the present invention inhibit or prevent pathological vascular conditions. In certain embodiments, the bioactive agents have anti-inflammatory properties, inhibit proliferation of smooth muscle cells, and/or influence gene expression in vascular tissue. In one embodiment, the bioactive agent is dexamethasone. Dexamethasone is considered both a smooth muscle cell anti-proliferative agent and an anti-inflammatory agent.

In an embodiment of the present invention, a need for treating one or more vascular structures is determined. The vascular structure, or other body fluid conduit, designated for treatment is surgically exposed using conventional techniques. Once the vascular structure is surgically exposed, means for stopping blood flow in the structure are applied to isolate the structure, thus defining the vascular treatment site. Such means include, but are not limited to, ligatures, ties, clamps, sutures, staples, or other devices capable of applying a compressive force to a vascular structure sufficient to stop flow of blood in the vascular structure.

The vascular treatment site is accessed with a needle-containing syringe and any blood or other fluid residing in the vascular treatment site is removed through the needle-containing syringe.

A thixotropic, turbid, bioactive agent-containing gel material, prepared as described herein, is placed in a needle-containing syringe. To administer the gel material to a vascular treatment site at a vascular structure, the open end of the needle is inserted inside the exsanguinated, vascular treatment site, and the gel material is injected inside the vascular structure and allowed to reside for a determined dwell time. As shear force is applied to the gel material during injection, the viscosity of the gel material decreases and the gel material flows through the needle into the interior space (luminal space) of the vascular treatment site. As the gel material fills the vascular treatment site, the shear forces applied to the gel material during injection diminish. As shear forces on the gel material diminish, the viscosity of the gel material increases, and the gel material will not flow under the influence of its own weight.

Once the gel material is inside a vascular treatment site, any bioactive agents associated with the gel material can move from the gel material to tissues of the vascular treatment site. The delivery of bioactive agent from the gel material to vascular tissue can occur within a range of about 5 seconds to greater than about one hour (see e.g. Example 4, infra). The dwell time of the gel material can be chosen to be longer than is needed to deliver sufficient amounts of bioactive agent to vascular tissue of a vascular treatment site to treat a vascular condition.

Following a dwell time sufficient for substantial bioactive agent to be delivered to a vascular treatment site to treat the vascular tissue, the means for stopping blood flow in the isolated vascular structure are removed. Once the means are removed, flowing blood through the vascular treatment site is re-established. As flowing blood is re-established in the vascular treatment site, shear force is once again applied to the gel material. As shear force is applied to the gel material, the viscosity of the gel material is decreased causing the gel material to begin substantially dissolving in the flowing blood. If the isolated, exsanguinated, vascular treatment site is transparent or translucent, then substantial dissolution of the gel material in flowing blood can be observed through the vascular treatment site with the naked eye. Substantial dissolution of the gel material continues until essentially all the gel material is removed from the vascular treatment site and is substantially dissolved in the blood stream. The substantially dissolved gel material does not limit, occlude, or otherwise diminish blood flow in vascular structures located distally (i.e., downstream) to the vascular treatment site.

Once flowing blood is re-established in the treated vascular treatment site, the vascular treatment site is surgically closed, and any other necessary surgical procedures performed.

Another embodiment of the method of the present invention can be practiced using interventional techniques. Interventional techniques routinely involve minimally invasive procedures. Often this technique is initiated by a puncture or cut-down of a vascular structure and insertion of a catheter through an interventional access site into the vascular structure. Interventional access sites may include, but are not limited to, access through an implanted vascular prosthesis, brachial artery, carotid artery, iliac artery, femoral artery, aorta, and other arterial or venous sites.

After insertion of a catheter through an interventional access site into the vascular structure, the catheter can then be guided to a site with a vascular condition in need of vascular treatment (i.e., a vascular treatment site), from the interventional access site. The vascular treatment site may include, but is not limited to, vascular conduits such as a blood vessel, a vascular graft, a vascular stent, a vascular filter, a vascular anastomosis, and a vascular stent graft.

One embodiment of the method of the present invention relates to an interventional treatment of a vascular condition involving the administration of a gel material to a vascular treatment site by injection through a catheter. The gel material may be injected directly to the vascular treatment site with or without prior occlusion of flowing blood at the vascular treatment site.

Another embodiment of the present invention relates to catheter injection of a thixotropic, turbid, bioactive agent-containing gel material through a medical device, including, but not limited to, commercially available catheters, single balloon catheters, needle-studded catheters, infusion catheters, balloon catheters, double balloon catheters, angioplasty balloon, weeping balloon catheters, infusion balloon catheters, and needle studded balloon catheters.

In another embodiment, the thixotropic, turbid, bioactive agent-containing gel material may be pre-applied to an implantable medical device, vascular prosthesis, or catheter-based device prior to catheter insertion into a vascular structure. For example, the thixotropic, turbid, bioactive agent-containing gel material may be applied manually to an implantable medical device, vascular prosthesis, or catheter-based device including, but not limited to, a stent, stent graft, vascular graft, angioplasty balloon, needle studded balloon, and other vascular prosthesis. The application may be continuous or discontinuous, covering at least a portion of the implantable medical device. Interventional vascular access is then used to place the catheter-based device at a vascular treatment site. The catheter-based device is then placed at the vascular treatment site allowing for delivery of the thixotropic, turbid, bioactive agent-containing gel material to the vascular treatment site.

Figure 6A:
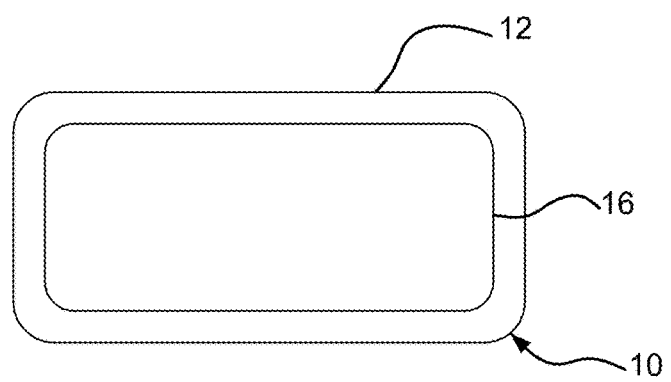
FIG. 6A shows a medical device having at least one thixotropic, turbid, gel material applied to at least a portion of the medical device.

FIG. 6A depicts a cross section of a medical device 16 as from a stent, stent-graft, graft, balloon, or other vascular prosthesis, having a thixotropic, turbid gel material 12 of the present invention applied to the medical device 16. Gel material 12 is applied to the entire surface of the medical device 16 to create an applied medical device 10. The application may be continuous or discontinuous.

Figure 6B:
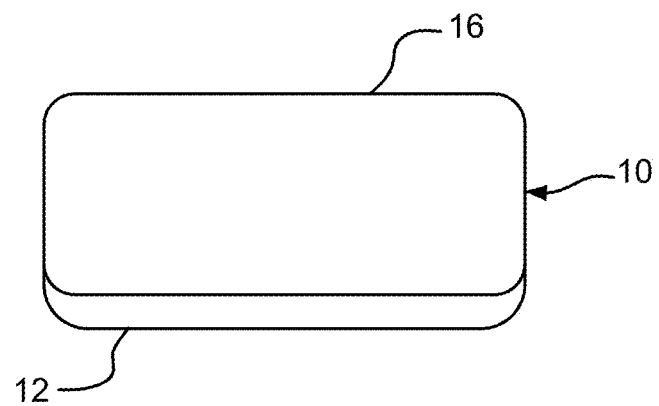
FIG. 6B shows a medical device having at least one thixotropic, turbid, gel material applied to at least a portion of the medical device.
Figure 6C:
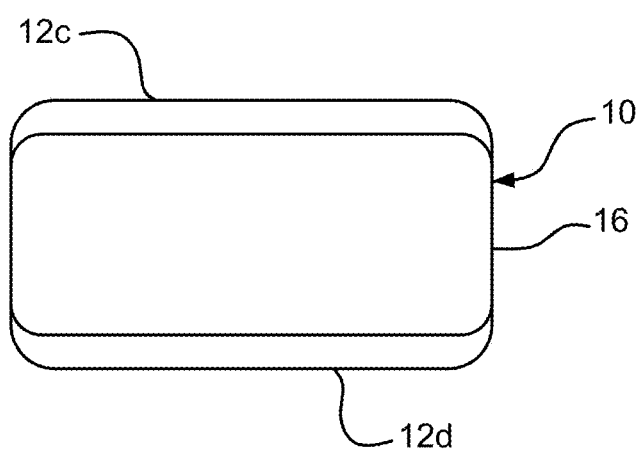
FIG. 6C shows a medical device having at least one thixotropic, turbid, gel material applied to at least a portion of the medical device.

FIG. 6B depicts a cross section of a medical device 16 as from a stent, stent-graft, graft, balloon, or other vascular prostheses, having a thixotropic, turbid gel material 12 of the present invention applied to the medical device 16. Gel material 12 is applied to one surface of the medical device 16 to create an applied medical device 10. The application may be continuous or discontinuous FIG. 6C depicts a cross section of a medical device 16, having a first application 12c and a second application 12d of the gel material of the present invention. Gel material 12c and 12d is applied to opposing sides of the medical device 16 to create an applied medical device 10. The application may be continuous or discontinuous.

In another embodiment, the thixotropic, turbid, bioactive agent-containing gel material may be pre-applied to a catheter-based device prior to catheter insertion into a vascular structure. For example, the thixotropic, turbid, bioactive agent-containing gel material may be applied manually to a catheter-based device including, but not limited to, a stent, stent graft, angioplasty balloon, needle studded balloon, and other vascular prosthesis. The application may be continuous or discontinuous, covering at least a portion of the implantable medical device. Catheter-based devices have a first diameter and a first surface area prior to and during insertion of the catheter-based devices into a vascular structure. After insertion into the vascular structure, the catheter-based devices are mechanically expanded to a second diameter and a second surface area within the vascular structure. The thixotropic properties of the gel materials permit the compositions to undergo changes in viscosity in response to the presence or absence of shear forces applied to the compositions. When a shear force is applied to the gel material during mechanical expansion of the catheter-based device, the viscosity of the composition is decreased to a point where the composition can readily deform from the first surface area to the second surface area as the catheter-based device is mechanically expanded. When the shear force is removed from the gel material after mechanical expansion of the catheter-based device, the viscosity of the composition is altered to a point where the composition will not flow under the influence of its own weight and will remain at the second surface area. The catheter-based device is placed at a vascular treatment site allowing for delivery of the thixotropic, turbid, bioactive agent-containing gel material to the vascular treatment site during and/or after expansion of the catheter-based device. A suitable gel material for use in the present invention is a material that can be made to flow under shear force, but exhibits no flow under the influence of its own weight under non-shear conditions.

Figure 7A:
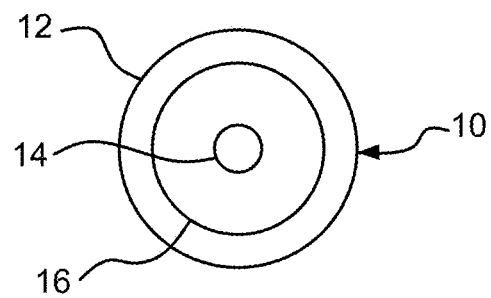
FIG. 7A shows a catheter-based device having at least one thixotropic, turbid, gel material applied to at least a portion of the catheter-based device.
Figure 7B:
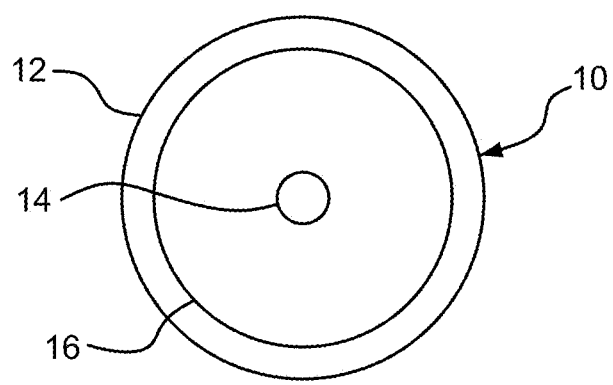
FIG. 7B shows a catheter-based device having at least one thixotropic, turbid, gel material applied to at least a portion of the catheter-based device.

FIG. 7A depicts a cross section of catheter-based device 16 as from a stent, stent-graft, balloon, or other vascular prosthesis, surrounding catheter 14, and having a thixotropic, turbid gel material 12 of the present invention applied to the catheter-based device 16. Gel material 12 is applied to a surface of catheter-based device 16 to create an applied catheter-based device 10 of a first diameter and a first surface area. The application may be continuous or discontinuous FIG. 7B depicts a cross section of the same catheter-based device shown by FIG. 7A, except that catheter-based device 16 is expanded to a second diameter and a second surface area.

In another embodiment, incorporation of a bioactive agent in the form of an angiographic contrast agent within the thixotropic, turbid, bioactive agent-containing gel material permits an angiographic visualization of the gel material at a vascular treatment site. The contrast agent may be incorporated within the thixotropic, turbid, bioactive agent-containing gel material through admixing, reformulation, combination, direct solubilization of the agent within the gel material, or other methods of incorporating said contrast agent in said gel material. These thixotropic, turbid, bioactive agent-containing gel materials are visualized at a vascular treatment site using angiography.

Other embodiments of thixotropic, turbid, bioactive agent-containing gel materials capable of treating vascular tissue in sufficient amounts to treat a vascular condition may include but are not limited to gel materials made from polyethylene glycol, α-cyclodextrin, hydroxypropyl-β-cyclodextrin (HPβCD), and a bioactive agent; polyvinyl alcohol, sodium borate, polyoxyethylene sorbitol ester, and a bioactive agent; sodium alginate, calcium chloride, hydroxypropyl-β-cyclodextrin, and a bioactive agent; and dextran, potassium chloride, hydroxypropyl-β-cyclodextrin (HPβCD), and a bioactive agent.

A preferred thixotropic, turbid, bioactive agent-containing gel material for use in the present invention is disclosed by Li et al. (U.S. Patent Application Publication 2002/0019369), which is incorporated herein by reference.

EXAMPLES

Example 1

This Example describes the preparation of a thixotropic, turbid gel material that contains a bioactive agent capable of treating vascular tissue in sufficient amounts to treat a vascular condition.

A first solution (referred herein as Solution 1A) was prepared by mixing phosphate buffered saline (PBS) (0.15M NaCl, pH 7.4, Invitrogen Corporation Carlsbad, Calif.) with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.), followed by adding dexamethasone (Pharmacia & Upjohn Company, Kalamazoo, Mich.) at 20 mg/ml with stirring and heating (60° C.). Solution 1A did not form a gel material and was not turbid.

A second solution (referred herein as Solution 1B) was prepared by dissolving polyethylene glycol (PEG, Dow Chemical, Midland, Mich.) of average Mn=8 kDa (0.26 g/ml) with PBS. Solution 1B did not form a gel material and was not turbid.

Equal volumes of Solution 1A and Solution 1B were combined with mixing to form Gel Material A. Gel Material A was turbid, and was opaque and white in appearance.

Example 2

This Example describes preparation of a thixotropic, turbid gel material that contains a bioactive agent capable of treating vascular tissue in sufficient amounts to treat a vascular condition.

A first solution (Solution 2A) was prepared by mixing PBS (0.15M NaCl, pH 7.4, Invitrogen) with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.), followed by adding 17β-estradiol (20 mg/ml) (Sigma-Aldrich) by stirring and heating (60° C.). Solution 2A did not form a gel material and was not turbid.

A second solution (Solution 2B) was prepared by dissolving PEG (Dow Chemical, Midland, Mich.) of average Mn=8 kDa (0.26 g/ml) in PBS. Solution 2B did not form a gel material and was not turbid.

Equal volumes of Solution 2A and Solution 2B were combined with mixing to form Gel Material B. Gel Material B was turbid, and was opaque and white in appearance.

Example 3

This Example describes preparation of a thixotropic, turbid gel material that contains a bioactive agent capable of treating vascular tissue in sufficient amounts to treat a vascular condition.

A first solution (Solution 3A) was prepared by mixing PBS (0.15M NaCl, pH 7.4) with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.), followed by adding dicumarol (0.67 mg/ml) (Sigma-Aldrich) by stirring and heating (60° C.). Solution 3A did not form a gel material and was not turbid.

A second solution (Solution 3B) was prepared by dissolving of PEG (Dow) of average Mn=8 kDa (0.26 g/ml) in PBS. Solution 3B did not form a gel material and was not turbid.

Equal volumes of solutions 3A and 3B were combined with mixing to form Gel Material C. Gel Material C was turbid, and was opaque and white in appearance.

Example 4

This Example describes in vivo delivery of dexamethasone to venous tissue ("treated vascular tissue") according to a method of the present invention.

A thixotropic, turbid gel material (herein referred to as Gel Material 4A) was made by the following steps.

A first solution (referred herein as Solution 4A) was prepared by mixing phosphate buffered saline (PBS) (0.15M NaCl, pH 7.4, Invitrogen Corporation Carlsbad, Calif.) with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.). Solution 4A did not form a gel material and was not turbid.

Then, a dexamethasone mixture was made by combining tritium-labeled dexamethasone (Perkin Elmer, Waltham, Mass. and unlabeled dexamethasone (Pharmacia & Upjohn Company) at a ratio of approximately 18 µg/g. Solution 4B was formed by solubilizing approximately 20 mg/ml of the dexamethasone mixture in Solution 4A. Solution 4B did not form a gel material and was not turbid.

Solution 4C was prepared by dissolving polyethylene glycol (PEG, Dow Chemical, Midland, Mich.) of average Mn=8 kDa (0.26 g/ml) with PBS. Solution 4C did not form a gel material and was not turbid.

Equal volumes of Solution 4B and Solution 4C were combined with mixing to form Gel Material 4A. Gel Material 4A was turbid, and was opaque and white in appearance.

Healthy canines were anaesthetized. A five centimeter (5 cm) segment of canine femoral vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (1 to 3 ml) of Gel Material 4A was injected at the cannulation and allowed to contact the blood vessel lumen for a treatment period of two (2), ten (10), or forty (40) minutes. No leakage of the Gel Material 4A from any treated vessel segment was observed during the treatment period.

After the designated treatment period, the ties were removed from each blood vessel segment, and blood flow was permitted to resume in the vascular treatment site for one hour (1 hr). Canine veins are relatively transparent, enabling observation with the unaided eye of Gel Material 4A administration and removal from the vascular treatment site. Upon re-establishment of blood flow in the vascular treatment site, Gel Material 4A was observed to substantially dissolve within approximately one minute (1 min). After one hour (1 hr) of blood flow, the vascular treatment site was harvested and washed thoroughly with saline.

Tissue sections (approximately 1 cm in length) were taken from each vascular treatment site and digested overnight in five milliliters (5 ml) of Solvable digestion fluid (Perkin Elmer). Fifteen milliliters (15 ml) of HiSafe 2 (Perkin Elmer), a scintillation cocktail, was added to the tissue sections to permit scintillation counting and quantification of beta radiation emitted by the tritium-labeled dexamethasone within each section.

A second group of healthy canines was anaesthetized. Control vein sections (approximately 1 cm in length) were obtained from these canines. The control vein sections were digested overnight in 5 ml of Solvable digestion fluid (Perkin Elmer). Known amounts of tritium-labeled dexamethasone were added to the digestion fluid. Fifteen milliliters (15 ml) of HiSafe 2 (Perkin Elmer), was added to the control vein sections to permit scintillation counting and quantification of the beta-radiation emitted by the tritium-labeled dexamethasone within each control vein section.

A scintillation counter (Perkin Elmer) was used to measure the beta radiation (disintegrations per minute) emitted by each control vein section and to generate a linear standard curve of disintegrations per minute as a function of the tritium-labeled dexamethasone within each section. Radiation levels (disintegrations per minute) from the tissue section were then compared to the standard curve to calculate tritium-labeled dexamethasone retention. The total amount of dexamethasone retained in each tissue section was determined by correlation of the total amount of dexamethasone in Gel Material 4A to the measured amount of tritium-labeled dexamethasone in each experimental tissue section.

FIG. 1 shows the resulting amount of total dexamethasone in the experimental tissue sections. As shown, when Gel Material 4A containing dexamethasone was allowed to contact a blood vessel lumen devoid of blood for two minutes (2 min), an average of 9.3 µg dexamethasone/g tissue remained in the tissue section after 1 h blood flow. The vascular treatment site included the tissue sections. Therefore, an average of 9.3 µg dexamethasone/g tissue was retained at the vascular treatment site at 1 h.

Example 5

This Example demonstrates the use of a thixotropic, turbid gel material in canine jugular veins ("treated vascular tissue"). This example also illustrates dissolution of a gel material in the blood stream that does not occlude vascular structures upon introduction to flowing blood.

Healthy canines were anaesthetized. A five centimeter (5 cm) segment of canine jugular vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. Three to four milliliters (3 to 4 ml) of Gel Material A (described in Example 1, supra) was injected at the cannulation and allowed to contact the blood vessel lumen for a treatment period of forty (40) minutes. No leakage of the Gel Material A from any treated vessel segment was observed during the treatment period.

After the designated treatment period, the ties were removed from each blood vessel segment, and blood flow was permitted to resume in the vascular treatment site for one hour (1 hr). Canine veins are relatively transparent, enabling observation with the unaided eye of Gel Material A administration and removal from the vascular treatment site. Upon re-establishment of blood flow in the vascular treatment site, Gel Material A was observed to substantially dissolve within approximately one minute (1 min). All canines remained in-life for one hour (1 h) after re-establishment of blood flow in treatment site.

After one hour (1 hr) of blood flow, the vascular treatment site was harvested and washed thoroughly with saline. Upon visible inspection, no Gel Material A was observable on luminal surfaces of any treatment site. Tissue sections (approximately 1 cm in length) were taken from each vascular treatment site. A histological examination (see FIG. 2) of these sections revealed a normal appearance of these sections.

The heart and lungs of canines treated with Gel Material A in the present Example were surgically excised. A pathological examination of the heart and lungs revealed no evidence of embolism or occlusion in these organs, indicating that Gel Material A dissolution in the blood stream did not limit blood flow in vascular structures located distal (i.e., downstream) to the vascular tissue treatment site. These results demonstrate that the method of administering the gel material did not occlude vascular structures upon introduction into flowing blood.

Example 6

This Example demonstrates the use of a thixotropic, turbid gel material in canine femoral veins ("treated vascular tissue"). This example also illustrates dissolution of a gel material in the blood stream that does not occlude vascular structures upon introduction to flowing blood.

Healthy canines were anaesthetized. A five centimeter (5 cm) segment of canine femoral vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (1 to 3 ml) of Gel Material A (described in Example 1, supra) was injected at the cannulation and allowed to contact the blood vessel lumen for a treatment period of forty (40) minutes. No leakage of the Gel Material A from any treated vessel segment was observed during the treatment period.

After the designated treatment period, the ties were removed from each blood vessel segment, and blood flow was permitted to resume in the vascular treatment site. Canine veins are relatively transparent, enabling observation with the unaided eye of Gel Material A administration and removal from the vascular treatment site. Upon re-establishment of blood flow in the vascular treatment site, Gel Material A was observed to substantially dissolve within approximately one minute (1 min).

After re-establishment of blood flow in the treatment site, subcutaneous tissue and skin surrounding the treatment site were closed with sutures. All canines remained in-life for fourteen days (14 d).

Figure 3:
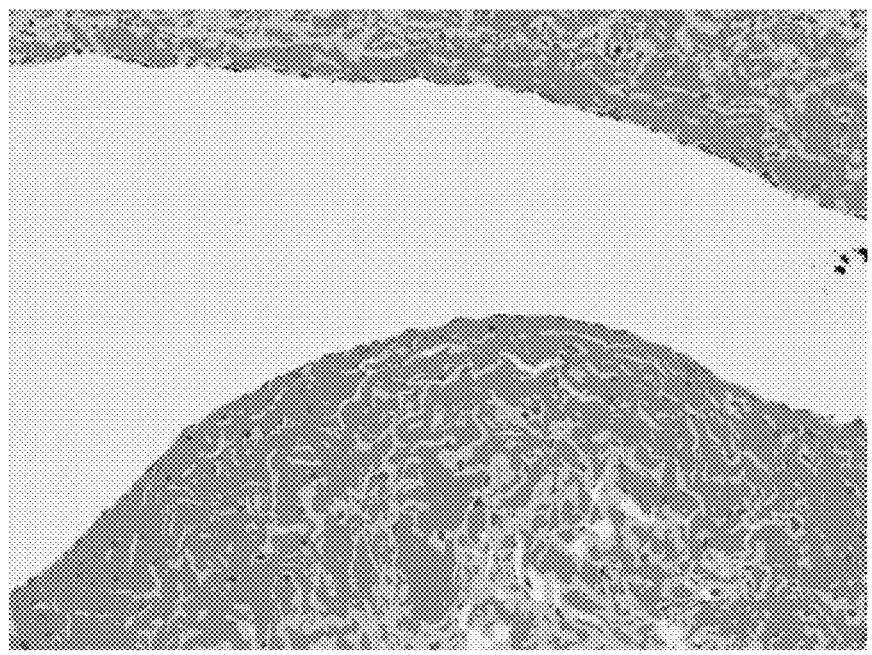
FIG. 3 shows two photographs (a) and (b), each containing histological data.
Figure 3:
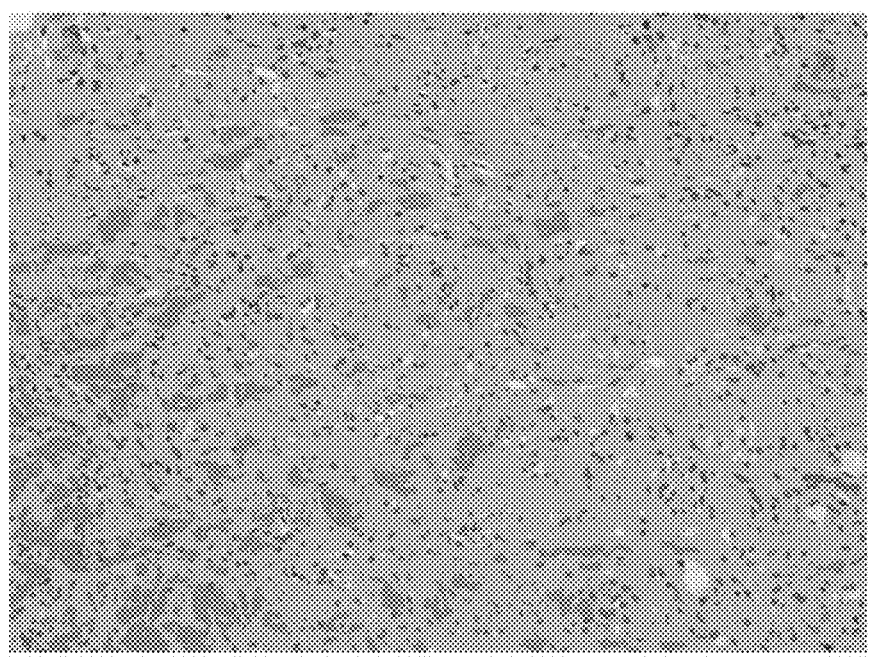

After fourteen days (14 d), all canines were euthanized. Then, the vascular treatment site was harvested and washed thoroughly with saline. Upon visible inspection, no Gel Material A was observable on luminal surfaces of any treatment site. Tissue sections (approximately 1 cm in length) were taken from each vascular treatment site. Histological examination of these sections indicated evidence of a pharmacological effect of the delivered dexamethasone. Specifically, a delayed healing response to the surgical trauma of vein cannulation was observed. Tissue sections from uncannulated lengths of the vascular treatment site displayed normal morphology as show in FIG. 3. These findings demonstrated the ability of thixotropic, turbid, bioactive agent-containing gel materials to deliver an effective amount of a biological agent to a vascular treatment site.

The heart and lungs of canines treated with Gel Material A in the present Example were also surgically excised at the time of euthanasia. A pathological examination of the heart and lungs revealed no evidence of embolism or occlusion in these organs, indicating that Gel Material A dissolution in the blood stream did not limit blood flow in vascular structures located distal (i.e., downstream) to the vascular tissue treatment site. These results demonstrate that the method of administering the gel material did not occlude vascular structures upon introduction into flowing blood.

Example 7

This Example describes in vivo delivery of estradiol to venous tissue ("treated vascular tissue") according to a method of the present invention.

A thixotropic, turbid gel material (herein referred to as Gel Material 7A) was made by the following steps.

A first solution (referred herein as Solution 7A) was prepared by mixing phosphate buffered saline (PBS) (0.15M NaCl, pH 7.4, Invitrogen Corporation Carlsbad, Calif.) with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.). Solution 7A did not form a gel material and was not turbid.

Then, an estradiol mixture was made by combining tritium-labeled estradiol (Perkin Elmer) and unlabeled estradiol (Sigma) at a ratio of approximately 27 μg/g. A second solution (referred herein as Solution 7B) was formed by solubilizing approximately 20 mg/ml of the estradiol mixture in Solution 7A. Solution 7B did not form a gel material and was not turbid.

A third solution (referred herein as Solution 7C) was prepared by dissolving polyethylene glycol (PEG, Dow Chemical) of average Mn=8 kDa (0.26 g/ml) with PBS. Solution 7C did not form a gel material and was not turbid.

Equal volumes of Solution 7B and Solution 7C were combined with mixing to form Gel Material 7A. Gel Material 7A was turbid, and was opaque and white in appearance.

Healthy canines were anaesthetized. A five centimeter (5 cm) segment of canine left femoral vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (1 to 3 ml) of Gel Material 7A was injected at the cannulation and allowed to contact the blood vessel lumen for a treatment period of forty (40) minutes. No leakage of the Gel Material 7A from any treated vessel segment was observed during the treatment period.

After the designated treatment period, the ties were removed from each blood vessel segment, and blood flow was permitted to resume in the vascular treatment site. Canine veins are relatively transparent, enabling observation with the unaided eye of Gel Material 7A administration and removal from the vascular treatment site. Upon re-establishment of blood flow in the vascular treatment site, Gel Material 7A was observed to substantially dissolve within approximately one minute (1 min).

After re-establishment of blood flow in the treatment site, subcutaneous tissue and skin surrounding the treatment site were closed with sutures. All canines remained in-life for fourteen days (14 d).

After fourteen days (14 d), all canines treated previously with Gel Material 7A were again anaesthetized. The vascular treatment site from the left femoral vein of each canine was then harvested and washed thoroughly with saline.

With the canines still remaining in-life, a five centimeter (5 cm) segment of the contralateral right femoral vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (1 to 3 ml) of Gel Material 7A was injected at the cannulation and allowed to contact the blood vessel lumen for a treatment period of forty (40) minutes. No leakage of the Gel Material 7A from any treated vessel segment was observed during the treatment period.

After the designated treatment period, the ties were removed from each blood vessel segment, and blood flow was permitted to resume in the vascular treatment site for one hour (1 h). Canine veins are relatively transparent, enabling observation with the unaided eye of Gel Material 7A administration and removal from the vascular treatment site. Upon re-establishment of blood flow in the vascular treatment site, Gel Material 7A was observed to substantially dissolve within approximately one minute (1 min).

After one hour (1 hr) of blood flow, the vascular treatment site from the right femoral vein was harvested and washed thoroughly with saline.

Tissue sections (approximately 1 cm in length) were taken from all vascular treatment sites (from the left and right femoral veins) and digested overnight in five milliliters (5 ml) of Solvable digestion fluid (Perkin Elmer). Fifteen milliliters (15 ml) of HiSafe 2 (Perkin Elmer), a scintillation cocktail, was added to the tissue sections to permit scintillation counting and quantification of beta radiation emitted by the tritium-labeled estradiol within each section.

A second group of untreated, healthy canines were anaesthetised. Control vein sections (approximately 1 cm in length) were obtained from these canines. The control vein sections were digested overnight in 5 ml of Solvable digestion fluid (Perkin Elmer). Known amounts of tritium-labeled estradiol were added to the digestion fluid. Fifteen milliliters (15 ml) of HiSafe 2 (Perkin Elmer), was added to the control vein sections to permit scintillation counting and quantification of the beta-radiation emitted by the tritium-labeled estradiol within each control vein section.

A scintillation counter (Perkin Elmer) was used to measure the beta radiation (disintegrations per minute) emitted by each control vein section and to generate a linear standard curve of disintegrations per minute as a function of the tritium-labeled estradiol within each section. Radiation levels (disintegrations per minute) from the tissue section were then compared to the standard curve to calculate tritium-labeled estradiol retention. The total amount of estradiol retained in each tissue section was determined by correlation of the total amount of estradiol in Gel Material 7A to the measured amount of tritium-labeled estradiol in each experimental tissue section.

FIG. 4 shows the resulting amount of total estradiol in the experimental tissue sections. As shown, when Gel Material 7A containing estradiol was allowed to contact a blood vessel lumen devoid of blood for 40 minutes (40 min), an average of 9.8 µg estradiol/g tissue remained in the tissue section after one hour (1 h blood flow). The vascular treatment site included the tissue sections. Therefore, an average of 9.8 µg estradiol/g tissue was retained in the vascular treatment site at 1 h.

As shown in FIG. 4, when Gel Material 7A containing estradiol was allowed to contact a blood vessel lumen devoid of blood for 40 minutes (40 min), an average of 0.3 µg estradiol/g tissue remained in the tissue section after fourteen days (14 d). The vascular treatment site included the tissue sections. Therefore, an average 0.3 µg estradiol/g tissue was retained in the vascular treatment site at fourteen days (14 d).

Example 8

This Example describes preparation of a thixotropic, turbid gel material that contains a first bioactive agent capable of treating vascular tissue in sufficient amounts to treat a vascular condition and a second bioactive agent in the form of a phase contrast agent to assist angiographic visualization of the gel material. This example demonstrates visualization of the gel material using angiography.

A first solution (referred herein as Solution 8A) was prepared by mixing PBS with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich, St. Louis, Mo.) through stirring and heating (60° C.), followed by adding dexamethasone at 20 mg/ml and 600 mg/ml of iohexol (Hovione, Loures, Portugal) with stirring and heating (60° C.). Solution 8A did not form a gel material and was not turbid.

A second solution (referred herein as Solution 8B) was prepared by dissolving PEG of average Mn=8 kDa (0.26 g/ml) with PBS. Solution 8B did not form a gel material and was not turbid.

Equal volumes of Solution 8A and Solution 8B were combined with mixing to form Gel Material D. Gel Material D was turbid, and was opaque and white in appearance.

Figure 5:
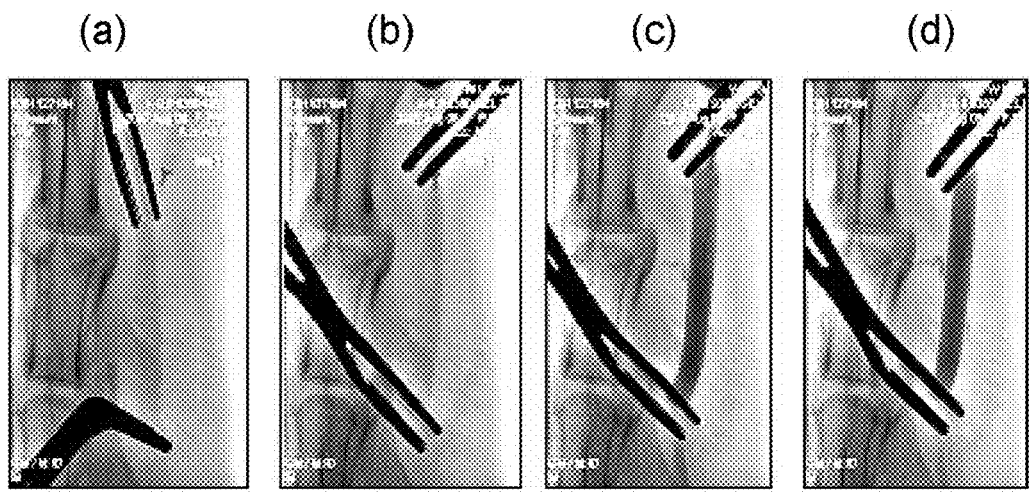
FIG. 5 shows four photographs (a), (b), (c), and (d).

A healthy canine was anaesthetized. A segment of canine jugular vein, approximately five centimeters (5 cm) in length, was surgically exposed. Blood flow in the segment was stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of Gel Material D was injected at the cannulation and visualized by angiography (FIG. 5c).

After angiography, the clamps were removed from the blood vessel segment, and blood flow was permitted to resume in the vascular treatment site for approximately five minutes (5 min). Then, blood flow in the segment was again stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of Gel Material A (as described in Example 1, supra, and which contained no phase contrast agent) was injected at the cannulation and visualized by angiography (FIG. 5b) as a control.

After angiography, the clamps were removed from the blood vessel segment, and blood flow was permitted to resume in the vascular treatment site for approximately five minutes (5 min). Then, blood flow in the segment was again stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of saline (Sigma) was injected at the cannulation and visualized by angiography (FIG. 5a) as a control.

This example demonstrates visualization of the thixotropic turbid gel material using angiography.

Example 9

This Example describes preparation of a thixotropic, turbid gel material that contains a first bioactive agent capable of treating vascular tissue in sufficient amounts to treat a vascular condition and a second bioactive agent in the form of a phase contrast agent to assist angiographic visualization of the gel material. This example demonstrates visualization of the gel material using angiography.

A first solution (referred herein as Solution 9A) was prepared by mixing PBS with 0.40 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich, St. Louis, Mo.) through stirring and heating (60° C.), followed by adding dexamethasone at 20 mg/ml and 600 mg/ml of iopamidol (Hovione, Loures, Portugal) with stirring and heating (60° C.). Solution 9A did not form a gel material and was not turbid.

A second solution (referred herein as Solution 9B) was prepared by dissolving PEG of average Mn=8 kDa (0.26 g/ml) with PBS. Solution 9B did not form a gel material and was not turbid.

Equal volumes of Solution 9A and Solution 9B were combined with mixing to form Gel Material E. Gel Material E was turbid, and was opaque and white in appearance.

A healthy canine was anaesthetized. A segment of canine jugular vein, approximately five centimeters (5 cm) in length, was surgically exposed. Blood flow in the segment was stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of Gel Material E was injected at the cannulation and visualized by angiography (FIG. 5d).

After angiography, the clamps were removed from the blood vessel segment, and blood flow was permitted to resume in the vascular treatment site for approximately five minutes (5 min). Then, blood flow in the segment was again stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of Gel Material A (as described in Example 1, supra, and which contained no phase contrast agent) was injected at the cannulation and visualized by angiography (FIG. 5b) as a control.

After angiography, the clamps were removed from the blood vessel segment, and blood flow was permitted to resume in the vascular treatment site for approximately five minutes (5 min). Then, blood flow in the segment was again stopped by constriction of the vein with clamps positioned at the proximal and distal ends of the segment. A vascular tissue treatment site was the length of vessel between the clamps. The vascular treatment site was cannulated. Blood within the vessel lumen was withdrawn at the cannulation using a syringe. One to three milliliters (3 to 4 ml) of saline (Sigma) was injected at the cannulation and visualized by angiography (FIG. 5a) as a control.

This example demonstrates visualization of the thixotropic turbid gel material using angiography.

Example 10

This Example describes delivery through a medical device of a thixotropic, turbid gel material containing a bioactive agent capable of treating vascular tissue in sufficient amounts to inhibit a vascular condition.

Gel Material A (as described in Example 1, supra) was injected through three different medical devices under hand compression of a syringe attached to each medical device: a 4 French catheter (100 cm in length) (Cordis, Warren, N.J.); a 6 French catheter (90 cm in length) (Cordis); and a 20 Gauge needle (2.54 cm in length) (Monoject, Mansfield, Mass.). The medical device was attached to a five milliliter (5 ml) luer lock syringe (Becton Dickinson, Franklin Lakes, N.J.). Gel Material A passed through all three medical devices with hand compression of the attached syringe. This example demonstrates the method of administering the gel material by injection through a needle. This example also demonstrates the method of administering the gel material by endovascular delivery via a catheter.

Example 11

This Example describes in vivo delivery of dexamethasone to arterial tissue ("treated vascular tissue") according to a method of the present invention.

A thixotropic, turbid gel material (herein referred to as Gel Material 11A) was made by the following steps.

A first solution (referred herein as Solution 11A) was prepared by mixing phosphate buffered saline (PBS) (0.15M NaCl, pH 7.4, Invitrogen Corporation Carlsbad, Calif.) with 0.57 g/ml hydroxypropyl-β-cyclodextrin (HPβCD) (Sigma-Aldrich, St. Louis, Mo.) and 0.20 g/ml alpha-cyclodextrin (αCD) (Sigma-Aldrich) through stirring and heating (60° C.). Solution 11A did not form a gel material and was not turbid.

Then, a dexamethasone mixture was made by combining tritium-labeled dexamethasone (Perkin Elmer, Waltham, Mass. Perkin Elmer) and unlabeled dexamethasone (Pharmacia & Upjohn Company) at a ratio of approximately 9 µg/g. Solution 11B was formed by solubilizing approximately 20 mg/ml of the dexamethasone mixture in Solution 11A. Solution 11B did not form a gel material and was not turbid.

Solution 11C was prepared by dissolving polyethylene glycol (PEG, Dow Chemical, Midland, Mich.) of average Mn=8 kDa (0.26 g/ml) with PBS. Solution 11C did not form a gel material and was not turbid.

Equal volumes of Solution 11B and Solution 11C were combined with mixing to form Gel Material 11A. Gel Material 11A was turbid, and was opaque and white in appearance.

Healthy canines were anaesthetized. A five centimeter (5 cm) segment of canine femoral artery was surgically exposed. Blood flow in the segment was stopped by constriction of the artery with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (1 to 3 ml) of Gel Material 11A was injected at the cannulation and allowed to contact the blood vessel lumen for a treatment period of two (2) minutes. No leakage of the Gel Material 11A from any treated vessel segment was observed during the treatment period.

After the designated treatment period, the ties were removed from each blood vessel segment, and blood flow was permitted to resume in the vascular treatment site for one hour (1 hr). Canine arteries are relatively transparent, enabling observation with the unaided eye of Gel Material 11A administration and removal from the vascular treatment site. Upon re-establishment of blood flow in the vascular treatment site, Gel Material 11A was observed to substantially dissolve within approximately one minute (1 min).

After approximately one hour (1 hr) of blood flow, post-injection contrast angiography was performed to demonstrate the patency of capillaries and other vascular structures located distal to the treatment site after Gel Material 11A dissolution in the blood stream. Angiography of arteries distal to the treatment site demonstrated normal blood perfusion after gel material dissolution in the blood stream. These results demonstrate that the method of administering the gel material did not occlude vascular structures upon introduction into flowing blood.

Following angiography, the vascular treatment site was harvested and washed thoroughly with saline. Tissue sections (approximately 1 cm in length) were taken from each vascular treatment site and digested overnight in five milliliters (5 ml) of Solvable digestion fluid (Perkin Elmer). Fifteen milliliters (15 ml) of HiSafe 2 (Perkin Elmer), a scintillation cocktail, was added to the tissue sections to permit scintillation counting and quantification of beta radiation emitted by the tritium-labeled dexamethasone within each specimen.

A second group of healthy canines was anaesthetised. Control artery sections (approximately 1 cm in length) were obtained from these canines. The control artery sections were digested overnight in 5 ml of Solvable digestion fluid (Perkin Elmer). Known amounts of tritium-labeled dexamethasone were added to the digestion fluid. Fifteen milliliters (15 ml) of HiSafe 2 (Perkin Elmer), was added to the control artery sections to permit scintillation counting and quantification of the beta-radiation emitted by the tritium-labeled dexamethasone within each control artery section.

A scintillation counter (Perkin Elmer) was used to measure the beta radiation (disintegrations per minute) emitted by each control artery section and to generate a linear standard curve of disintegrations per minute as a function of the tritium-labeled dexamethasone within each section. Radiation levels (disintegrations per minute) from the tissue section were then compared to the standard curve to calculate tritium-labeled dexamethasone retained in the tissue section. The total amount of dexamethasone retained in each tissue section was determined by correlation of the total amount of dexamethasone in Gel Material 11A to the measured amount of tritium-labeled dexamethasone in each experimental tissue section.

When Gel Material 11 A containing dexamethasone was allowed to contact a blood vessel lumen devoid of blood for two minutes (2 min), an average of 9.1 µg dexamethasone/g tissue was retained in each tissue section after one hour (1 h) blood flow. The vascular treatment site included the tissue sections. Therefore, an average of 9.1 µg dexamethasone/g tissue was retained in the vascular treatment site at one hour (1 h).

Example 12

This Example describes preparation of a thixotropic, turbid gel material that contains a bioactive agent capable of treating vascular tissue in sufficient amounts to treat a vascular condition.

A thixotropic, turbid gel material (herein referred to as Gel Material F) made from polyvinyl alcohol (PVA, Spectrum, Gardena, Calif.), sodium borate (Borax, Sigma), polyoxyethylene sorbitol ester (Tween®20, Sigma), and dexamethasone (Pharmacia & Upjohn Company) was made by the following steps.

Three solutions were separately formed:
Solution 12A: 0.03 g PVA per milliliter water
Solution 12B: 10 mg dexamethasone per milliliter polyoxyethylene sorbitol ester
Solution 12C: 10 mg borax per milliliter water Then, 0.5 ml of Solution 12B was thoroughly mixed with 9.5 ml Solution 12A to form Solution 12D. Next, 0.5 ml of Solution 12C was added to 5 ml of Solution D. Upon mixing, a Gel Material F was formed and was turbid.

Example 13

This Example describes preparation of a thixotropic, turbid gel material that contains a bioactive agent capable of treating vascular tissue in sufficient amounts to treat a vascular condition.

A thixotropic, turbid gel material (herein referred to as Gel Material G) made from polyvinyl alcohol (PVA, Spectrum, Gardena, Calif.) and sodium borate (Borax, Sigma), and HPβCD (Sigma), and dexamethasone (Pharmacia & Upjohn Company) was made by the following steps.

Three solutions were separately formed:
Solution 13A: 0.05 g PVA per milliliter water
Solution 13B: 0.20 g HPβCD per milliliter
Solution 13C: 10 mg borax per milliliter water Then, Solution 13D was formed by solubilizing approximately 12 mg dexamethasone per milliliter in Solution 13B. Next, 2.5 ml Solution 13A, 2.5 ml Solution 13D, and 0.25 ml Solution 13C were thoroughly combined. Upon mixing, a Gel Material G was formed and was turbid.

Example 14

This Example describes in vivo delivery of dexamethasone to venous tissue ("treated vascular tissue") according to a method of the present invention using Gel Material G as described in Example 13.

Healthy canines were anaesthetized. A five centimeter (5 cm) segment of canine jugular vein was surgically exposed. Blood flow in the segment was stopped by constriction of the vein with rubber ties positioned at the proximal and distal ends of the segment. A vascular tissue treatment site was the length of vessel between the rubber ties. The vascular treatment site was cannulated. Blood within the vessel lumen was withdrawn at the cannulation using a syringe. The lumen of the vascular treatment site was irrigated three times with saline applied with a syringe at the cannulation. One to three milliliters (3 to 4 ml) of Gel Material G was injected at the cannulation and allowed to contact the blood vessel lumen for a treatment period of forty (40) minutes. No leakage of the Gel Material G from any treated vessel segment was observed during the treatment period.

After the designated treatment period, the ties were removed from each blood vessel segment, and blood flow was permitted to resume in the vascular treatment site for one hour (1 hr). Canine veins are relatively transparent, enabling observation with the unaided eye of Gel Material G administration and removal from the vascular treatment site. Upon re-establishment of blood flow in the vascular treatment site, Gel Material G was observed to substantially dissolve within approximately one minute (1 min). After one hour (1 hr) of blood flow, the vascular treatment site was harvested and washed thoroughly with saline.

Tissue sections (approximately 1 cm in length) were taken from each vascular treatment site. A histological examination of these sections revealed a normal appearance of these sections. Three additional sections of the vascular treatment site were analyzed for dexamethasone content by tissue extraction and quantified with high performance liquid chromatography combined with dual mass spectroscopy. Dexamethasone levels in these tissue sections were approximately 15.9±9.8 µg per gram tissue, demonstrating that the method of the present invention delivers a bioactive agent to a vascular tissue treatment site.

Example 15

This Example describes the preparation of a thixotropic, turbid gel material that contains a bioactive agent capable of treating vascular tissue in sufficient amounts to treat a vascular condition.

A thixotropic, turbid gel material (herein referred to as Gel Material H) made from sodium alginate (Sigma), calcium chloride (Sigma), hydroxypropyl-β-cyclodextrin (HPβCD) (Sigma), and dexamethasone (Pharmacia & Upjohn Company) was made by the following steps.

Three solutions were separately formed:
Solution 15A: 1.7 mg calcium chloride per milliliter water
Solution 15B: 0.40 g HPβCD per milliliter water
Solution 15C: 20 mg sodium alginate per milliliter water Then, Solution 15D was formed by solubilizing approximately 20 mg dexamethasone per milliliter of Solution 15B. Next, 2.5 ml Solution 15A, 2.5 ml Solution 15D, and 2.5 ml Solution 15C were combined. Upon mixing, a Gel Material H was formed and was turbid.

Example 16

This Example describes the preparation of a thixotropic, turbid gel material that contains a bioactive agent capable of treating vascular tissue in sufficient amounts to treat a vascular condition.

A thixotropic, turbid gel material (herein referred to as Gel Material X) made from dextran (Mn=4 kDa, Sigma) and potassium chloride (Sigma) and hydroxypropyl-β-cyclodextrin (HPβCD) (Sigma), and dexamethasone (Pharmacia & Upjohn Company) is made by the following steps.

Two solutions are separately formed:
Solution 16A: 0.40 g HPβCD per ml water
Solution 16B: 0.22 g potassium chloride per g water Then, Solution 16C is formed by solubilizing 10 mg/ml dexamethasone in Solution 16A. Next, 0.5 g dextran is solubilized by 0.5 ml of Solution 16C. Finally, 0.5 ml Solution 16B is added. Upon mixing, Gel Material X is formed and was turbid.

Example 17

This Example describes characterization of a thixotropic, turbid gel material that contains a bioactive agent capable of treating vascular tissue in sufficient amounts to treat a vascular condition. Thixotropy of Gel Material A was demonstrated by rheometry.

The viscosity of Gel Material A was characterized over a range of shear rates using a rheometer (Model AR-G2, TA Instruments, New Castle, Del.). This analysis technique involved measurement of shear stress during shear rate "ramp up" and subsequent "ramp down." Samples were analyzed at 25° C. with a forty millimeter (40 mm) cone and plate geometry. About one milliliter (1 ml) of Gel Material A was injected from a needle-less syringe onto the plate and allowed to equilibrate for 3 minutes. Then, a shear "ramp up" step was performed, whereby the shear rate was increased from 0.1 to 1.0 $s^{-1}$ over two minutes (2 min). Subsequently, a "ramp down" step was performed, whereby the shear rate was decreased from 1.0 to 0.1 $s^{-1}$ over two minutes (2 min).

Apparent viscosity at each point was calculated as the ratio of shear stress to shear rate. Initial viscosity at 0.1 $s^{-1}$ was approximately 90 Pa·s. The viscosity of Gel Material A was observed to decrease with increasing shear (during the shear "ramp up"). At 1.0 $s^{-1}$, the viscosity of Gel Material A was approximately 17 Pa·s. As the shear rate was then decreased (the "ramp down" step), the viscosity of Gel Material A was seen to increase. At the conclusion of the ramp down step, the viscosity of Gel Material A at 0.1 s$^{-1}$ was approximately 55 Pa·s.

Example 18

This Example describes an implantable medical device having a thixotropic, turbid, gel material containing a bioactive agent capable of treating vascular tissue in sufficient amounts to treat a vascular condition applied to at least a portion of the implantable medical device.

The implantable medical device used in this example was in the form of a nitinol wire reinforced tube made of a porous, expanded, polytetrafluoroethylene (ePTFE) material obtained from W.L. Gore & Associates, Inc., Flagstaff, Ariz. under the tradename VIABAHN® Endoprosthesis. The tubular device was fifteen centimeters (15 cm) in length and six millimeters (6 mm) in diameter.

Gel Material A (described in Example 1, supra) was applied to an exterior surface of the implantable medical device using a needle-containing syringe. Once applied, the gel material was seen to adhere to the exterior surface of the implantable medical device.

The implantable medical device was mechanically expanded. Upon expansion, the implantable medical device expanded from a first diameter and a first surface area to a second diameter and a second surface area. A substantial portion of Gel Material A applied to the exterior surface of the implantable medical device was seen to remain adherent to the exterior surface of the implantable medical device during expansion of the implantable medical device.

Example 19

This Example describes an implantable medical device having a thixotropic, turbid, gel material containing a bioactive agent capable of treating vascular tissue in sufficient amounts to treat a vascular condition applied to at least a portion of the implantable medical device.

The implantable medical device used in this example was in the form of a catheter-based device. The catheter-based device was in the form of an endovascular angioplasty balloon (POWERFLEX® P3, Cat. No. 420-4040L, Cordis Corporation). The restraining sheath of the balloon was removed from the implantable medical device. Then, Gel Material A (described in Example 1, supra) was applied to an exterior surface of the balloon of the implantable medical device using a needle-containing syringe. Once applied, the gel material was seen to adhere to the exterior surface of the balloon.

The balloon was mechanically expanded according to instructions for use provided with the packaging. Upon mechanical expansion, the balloon expanded from a first diameter and a first surface area to a second diameter and a second surface area. A substantial portion of Gel Material A applied to the exterior surface of the implantable medical device was seen to remain adherent to the exterior surface of the implantable medical device during and after mechanical expansion of the implantable medical device.

What is claimed is:

1. A method of treating a vascular condition comprising:
   accessing a vascular treatment site within an interior space of a continuous vascular structure by penetrating a wall of the continuous vascular structure with a syringe such that a tip of the syringe is located at the vascular treatment site;
   administering a gel material to the vascular treatment site within the interior space of the continuous vascular structure using the syringe, the gel material including a thixotropic, turbid gel containing hydroxypropyl-β-cyclodextrin (HPβCD), alpha-cyclodextrin (αCD), and at least one bioactive agent that is at least one of an anticoagulant and an anti-proliferative;
   allowing the gel material to remain at the vascular treatment site for a dwell time sufficient to release the bioactive agent from the gel material into the vascular tissue to treat the vascular tissue; and
   removing the gel material from within the interior space of the continuous vascular structure by applying a shear force to the gel material by allowing blood flow through the interior space of the continuous vascular structure such that a viscosity of the gel material is decreased, wherein the gel material substantially dissolves within one minute after applying the shear force.

2. The method of claim 1 wherein the gel material does not occlude the continuous vascular structure upon introduction into flowing blood.

3. The method of claim 1 wherein the gel material is administered to the interior space of the continuous vascular structure across the wall of the continuous vascular structure using a needle of the syringe.

4. The method of claim 1 wherein the bioactive agent is selected from the group consisting of dexamethasone, estradiol, carvedilol, and cilostazol.

5. The method of claim 1 wherein the vascular condition is intimal hyperplasia.

6. The method of claim 1, further comprising:
   identifying the continuous vascular structure in need of treatment or repair;
   isolating the continuous vascular structure;
   applying a means for stopping blood flow in the continuous vascular structure prior to administering the gel material to the vascular treatment site;
   allowing the gel material to remain at the vascular treatment site for the dwell time sufficient to release the bioactive agent from the gel material; and
   removing the means for stopping blood flow.

7. The method of claim 1, wherein the gel material includes a polymer and a pharmacologically effective amount of the bioactive agent;
   wherein the polymer comprises at least one of a polyether, a polyol, and a polyanion,
   wherein the HPβCD, the αCD, and the polymer self-assemble to form a hydrogel by spontaneous association and are present in the gel material in respective amounts effective to make the hydrogel thixotropic and injectable into a body of a person through a needle; and
   wherein the hydrogel forms a matrix for the bioactive agent such that when the gel material is injected into the body of the person, the bioactive agent is released from the hydrogel in a sustained manner during the dwell time.

8. The method of claim 1, wherein the gel material is intravenously administered to the interior space of a unitary vascular structure having a continuous length.

9. The method of claim 1, wherein the gel material includes a beta-radiation emitting agent.

10. The method of claim 1, wherein administering the gel material to the vascular treatment site is carried out free of disruption to the continuous vascular structure proximate the vascular treatment site.

11. The method of claim 1, wherein the gel material is formed by mixing a first solution comprising the HPβCD, the αCD, and the at least one bioactive agent, and a second solution comprising polyethylene glycol.

12. A method of treating a vascular condition, the method comprising:
   endoluminally accessing a vascular treatment site from within a luminal space of a continuous vascular structure using a catheter;
   administering a gel material to the vascular treatment site within the luminal space of the continuous vascular structure with the catheter, wherein the continuous vascular structure is a unitary vessel having a continuous length, the gel material including a thixotropic, turbid gel containing hydroxypropyl-β-cyclodextrin (HPβCD), alpha-cyclodextrin (αCD), and at least one bioactive agent comprising at least one of an anticoagulant and an anti-proliferative such that a vascular tissue of the vascular treatment site is treated upon release of the bioactive agent from the gel;
   allowing the gel material to remain at the vascular treatment site for a dwell time sufficient to release the bioactive agent from the gel material into the vascular tissue such that the vascular condition in the vascular tissue is treated; and
   removing the gel material from within the luminal space of the vascular structure by providing a shear stress to the gel material such that a viscosity of the gel material is decreased, wherein the gel material substantially dissolves within one minute after providing the shear stress.

13. The method of claim 12 wherein the gel material does not occlude vascular structures upon introduction into flowing blood.

14. The method of claim 12, wherein the gel material includes a polymer and a pharmacologically effective amount of the bioactive agent;
   wherein the polymer comprises at least one of polyethylene glycol and polyvinyl alcohol;
   wherein the HPβCD, the αCD, and the polymer self-assemble to form a hydrogel by spontaneous association and are present in the hydrogel in respective amounts effective to make the hydrogel thixotropic and injectable into a body of a person through a needle; and
   wherein the hydrogel forms a matrix for the bioactive agent such that when the gel material is injected into the body of the person, the bioactive agent is released from the hydrogel in a sustained manner during the dwell time.

15. The method of claim 12 wherein administrating the gel material includes injection through one of a catheter and balloon or deploying a medical device comprising one of a stent-graft and a balloon onto which the gel material has been applied.

16. The method of claim 12, wherein administering the gel material to the vascular treatment site is carried out free of disruption to the continuous vascular structure proximate the vascular treatment site.

17. A method of treating a vascular condition, the method comprising:
   accessing a vascular treatment site within a luminal space of a continuous vascular structure without substantial mechanical or chemical trauma to the continuous vascular structure;
   administering a gel material to a vascular treatment site within the luminal space of the continuous vascular structure without substantial mechanical or chemical trauma to the continuous vascular structure, the gel material including a thixotropic, turbid, gel containing hydroxypropyl-β-cyclodextrin (HPβCD), alpha-cyclodextrin (αCD), and at least one bioactive agent;
   allowing the gel material to remain at the vascular treatment site for a dwell time sufficient to release the bioactive agent from the gel material into the vascular tissue, the bioactive agent having at least one of anticoagulant properties and anti-proliferative properties such that the vascular tissue is treated upon release of the bioactive agent from the gel material; and
   removing the gel material from within the luminal space of the continuous vascular structure by resuming blood flow through the interior space of the continuous vascular structure, wherein the gel material includes a hydrogel, and wherein the gel material is configured to substantially dissolve into flowing blood without occluding vascular structures located downstream of the vascular treatment site, wherein the gel material substantially dissolves within one minute after resumption of blood flow through the interior space of the continuous vascular structure.

18. The method of claim 17, wherein administering the gel material to the vascular treatment site includes delivering the gel material to the luminal space of the continuous vascular structure without cutting the continuous vascular structure proximate the vascular treatment site.

19. The method of claim 17, wherein the gel material further comprises polyethylene glycol.

* * * * *